US012806181B2

(12) United States Patent
Berlia

(10) Patent No.: US 12,806,181 B2
(45) Date of Patent: Nov. 24, 2026

(54) CONTROLLED RELEASE FORMULATIONS OF FLAVOXATE AND PROCESS FOR PREPARATION THEREOF

(71) Applicant: Flavostar LLC, Lewes, DE (US)

(72) Inventor: Sushma Paul Berlia, New Delhi (IN)

(73) Assignee: Flavostar LLC, Lewes, DE (US)

( * ) Notice: Subject to any disclaimer, the term of this patent is extended or adjusted under 35 U.S.C. 154(b) by 268 days.

(21) Appl. No.: 18/057,063

(22) Filed: Nov. 18, 2022

(65) Prior Publication Data

US 2023/0330076 A1 Oct. 19, 2023

(30) Foreign Application Priority Data

Nov. 19, 2021 (IN) ............................ 202111053299

(51) Int. Cl.

*A61K 31/453* (2006.01)
*A61K 9/00* (2006.01)
*A61K 9/20* (2006.01)
*A61K 9/24* (2006.01)

(52) U.S. Cl.

CPC .......... *A61K 31/453* (2013.01); *A61K 9/0053* (2013.01); *A61K 9/2018* (2013.01); *A61K 9/2031* (2013.01); *A61K 9/2054* (2013.01); *A61K 9/209* (2013.01); *A61K 9/2095* (2013.01)

(58) Field of Classification Search

CPC ........ A61K 9/20; A61K 31/4453; A61P 13/10
See application file for complete search history.

(56) References Cited

U.S. PATENT DOCUMENTS

| | | | | |
|---|---|---|---|---|
| 5,165,937 | A | 11/1992 | Santus et al. | |
| 5,328,903 | A | 7/1994 | Ishii et al. | |
| 6,346,532 | B1 | 2/2002 | Maruyama et al. | |
| 7,342,117 | B2 | 3/2008 | Kawazoe et al. | |
| 7,982,049 | B2 | 7/2011 | Kawazoe et al. | |
| RE44,872 | E | 4/2014 | Takasu et al. | |
| 8,772,315 | B2 | 7/2014 | Suzuki et al. | |
| 8,835,474 | B2 | 9/2014 | Takasu et al. | |
| 9,622,980 | B2 * | 4/2017 | Grenier et al. | A61K 31/4422 |
| 9,642,809 | B2 | 5/2017 | Hemmingsen et al. | |
| 9,655,885 | B2 | 5/2017 | Peddy et al. | |
| 9,750,701 | B2 | 9/2017 | Jans et al. | |
| 10,842,780 | B2 | 11/2020 | Takaishi et al. | |
| 11,707,451 | B2 | 7/2023 | Takaishi et al. | |
| 2017/0128379 | A1 | 5/2017 | Pilgaonkar et al. | |
| 2021/0052600 | A1 | 2/2021 | Kamo et al. | |
| 2021/0205619 | A1 | 7/2021 | Wong et al. | |

FOREIGN PATENT DOCUMENTS

| | | | | |
|---|---|---|---|---|
| EP | 0393572 | A2 | 10/1990 | |
| EP | 0250374 | B1 | 5/1991 | |
| EP | 3777853 | A1 | 2/2021 | |
| JP | S63154619 | A | 6/1988 | |
| JP | H03148215 | A | 6/1991 | |
| WO | WO 2007/010509 | A2 | 1/2007 | |
| WO | WO 2008/148798 | A2 | 12/2008 | |
| WO | WO 2009/013846 | A1 | 1/2009 | |
| WO | WO 2017/186593 | A1 | 11/2017 | |
| WO | WO 2017/186598 | A1 | 11/2017 | |
| WO | WO 2020/021422 | A1 | 1/2020 | |
| WO | WO2020021422 | * | 1/2020 | A61K 9/20 |
| WO | WO 2023/089553 | A1 | 5/2023 | |

OTHER PUBLICATIONS

Written Opinion of the International Searching Authority, of PCT/IB2022/061141, filed on Nov. 11, 2022, 8 pp.
Abreu-Mendes et al. (2020) "Pharmacology of the lower urinary tract: update on LUTS treatment", Therapeutic Advances in Urology, 12:1-16.
Blake-James et al. (2006) "The role of anticholinergics in men with lower urinary tract symptoms suggestive of benign prostatic hyperplasia: a systematic review and meta-analysis", BJU International, Blackwell Science, Hoboken, USA, 99(1):85-96.
Dash et al. (2010) "Efficacy and Safety of Tamsulosin With and Without Flavoxate in the Treatment of Symptomatic Benign Prostastic Hypoplasia: A Randomized, Single-Blind Study", Urotoday International Journal, 3(4), XP093347747 (6 pages).
International Patent Application No. PCT/IB2019/056223, filed Jul. 21, 2019, by Sushma Paul Berlia, International Search Report and Written Opinion of International Searching Authority, mailed Dec. 2, 2019.
International Patent Application No. PCT/US2025/046761, filed Sep. 17, 2025, by Flavostar LLC, International Search Report and Written Opinion of International Searching Authority, mailed Jan. 2, 2026.
International Patent Application No. PCT/US2025/046767, filed Sep. 17, 2025, by Flavostar Llc, International Search Report and Written Opinion of International Searching Authority, mailed Feb. 18, 2026.
Kato et al. (2008) "Clinical evaluation of supplemental administration of flavoxate hydrochloride in benign prostatic hyperplasia patients with nocturia resistant to an alpha1-adrenoceptor blocker", Hinyokika Kiyo., 54(3):173-177.
Niijima et al. (1981) "A multicenter clinical trial of flavoxate hydrochloride", Nishinippon Hinyokika, 43:1055-1063.
Rashid et al. (2021) "Development and evaluation of Flavoxate HCI double core compressed tablet formulations by swellable granulation technique", Acta Poloniae Pharmaceutica-Drug Research, 78(5):667-677.
Recordati Pharmaceuticals Limited (2020) "Urispas 200 mg Film-coated Tablets—Summary of Product Characteristics" (flavoxate hydrochloride), Revised Apr. 1, 2020 (4 pages).
Romancik et al. (2014) "Tamsulosin/solifenacin fixed-dose combination tablet for the treatment of male lower urinary tract symptoms", Drugs of Today, 50(12):803-811.
Ruffman (1988) "A review of flavoxate hydrochloride in the treatment of urge incontinence", J. Int Med Res., 16(5):317-330.
Satyavathi et al. (2014) "Formulation and development of Flavoxate hydrochloride ER capsules", IJPSR, 5(5):1949-1956.

(Continued)

*Primary Examiner* — Robert A Wax
*Assistant Examiner* — Kimberly Barber
(74) *Attorney, Agent, or Firm* — Finnegan, Henderson, Farabow, Garrett & Dunner, LLP

(57) ABSTRACT

The present disclosure relates to controlled or extended release formulations of Flavoxate or similar lipophilic acid soluble drugs. The disclosure also relates to methods for preparation of such formulations and uses thereof.

13 Claims, No Drawings

(56) References Cited

OTHER PUBLICATIONS

Schott et al. (1982) "The role of surfactants in the release of very slightly soluble drugs from tablets", Journal of Pharmaceutical Sciences, American Chemical Society and American Pharmaceutical Association, 71(9): 1038-1045.
Shyamala (2017) "Formulation Design, Development and Invitro Evaluation of Abacavir Sulphate Gastroretentive Microspheres"—J.K.K. Nattaraja College of Pharmacy Kumarapalayam—638183 TAMILNADU—REG. No. 261510262 (132 pages).
Zor et al. (2014) "Flavoxate in urogynecology: an old drug revisited", International Urogynecology Journal, 26(7):959-966.

* cited by examiner

CONTROLLED RELEASE FORMULATIONS OF FLAVOXATE AND PROCESS FOR PREPARATION THEREOF

RELATED APPLICATIONS

This application claims the benefit of priority to Indian Provisional Application No. 202111053299, filed Nov. 19, 2021, the disclosure of which is incorporated herein by reference in its entirety.

FIELD OF THE INVENTION

The present disclosure relates to controlled or extended release formulations of Flavoxate or similar lipophilic acid soluble drugs as bi-layered, multi-layered tablets, multi-coated mini-tablets, MUPS (Multiple Unit Pellet System) tablets, pellets or beads filled in capsules with biphasic drug release profile. The disclosure also relates to methods for preparation of such formulations and uses thereof.

BACKGROUND OF THE INVENTION

Oral ingestion is a convenient and commonly employed route of drug delivery due to its ease of administration, high patient compliance, cost effectiveness, reduced sterility constraints, and flexibility in the design of dosage form. However, the major challenge with oral dosage forms lies in their poor bioavailability.

2-piperidinoethyl 3-methylflavone-8-carboxylate hydrochloride (hereinafter referred to as Flavoxate or Flavoxate hydrochloride) is a flavonic derivative synthesized by Recordati Laboratories in 1960. Flavoxate is a spasmolytic drug with potent smooth muscle relaxant properties. It inhibits the phosphodiesterase enzyme and, by calcium antagonistic action, relaxes smooth muscle. The drug acts preferentially on the genitourinary tract and does not act on the intestine. It has both central and direct smooth muscle relaxant activity. It has local anaesthetic property as strong as lidocaine but no anticholinergic activity [M Zor, E Aydur, R R Dmochowski. Flavoxate in urogynecology: an old drug revisited. International Urogynecology Journal, 6 Dec. 2014, 26(7):959-966]. Using rat brain tissue, it has been shown to have only weak binding activity on receptors (α- and β-noradrenergic, muscarinic, serotoninergic and opiate receptors, and calcium binding sites) which are directly or indirectly involved in the nervous control of the lower urinary tract.

Flavoxate hydrochloride displays slight affinity to muscarinic receptors, having a median inhibitory concentration ($IC_{50}$) of 12.2 μm. This finding is in clear contrast to the strong binding to muscarinic receptors typical of anticholinergic agents, such as oxybutynin ($IC_{50}$ of 5.4 μm). It also helps to explain the low incidence and severity of typical anticholinergic clinical effects (dry mouth, tremor, blurred vision and tachycardia) which are shown by Flavoxate hydrochloride in the treatment of disorders of the lower urinary tract. In addition, the smooth muscle relaxing activity of Flavoxate hydrochloride reduces obstructive symptoms (hesitancy, intermittency, dribbling and retention) [R. Ruffmann. A Review of Flavoxate hydrochloride in the Treatment of Urge Incontinence, The Journal of International Medical Research 1988; 16: 317-330] and no undesirable increase in residual urine volume with Flavoxate occurs as is normally found when administering anticholinergics.

Flavoxate hydrochloride has been used therapeutically for symptomatic relief of pollakiuria, particularly nocturia, dysuria, urgency, vesicle suprapubic pain, frequency, and urinary incontinence originating from various pathological situations such as prostatitis, urethritis, cystitis, urethero-cystitis, uretherotrigonitis, and the side effects of radiotherapy or surgical therapy of the urinary tract. In addition, Flavoxate is indicated for the relief of vesico-urethral spasm due to catheterization, cystoscopy, or indwelling catheter, prior to cystoscopy or catheterization, or sequelae of surgical intervention of the lower urinary tract. Flavoxate is also used to relieve irritative symptoms of benign prostatic hyperplasia (BPH) and overactive bladder. The use of Flavoxate hydrochloride, however, is not restricted to the treatment of bladder dysfunctions only. Flavoxate hydrochloride as a drug is also used for treatment of premature labour and abdominal dysmenorrhoea pain. Renal colic has also been treated effectively with Flavoxate hydrochloride and the compound has also been administered as a supportive anti-spasmodic during extracorporeal (shock wave) lithotripsy.

Flavoxate as a drug is commercially available in strength of 100 mg and 200 mg sugar coated immediate release (IR) tablets. The therapeutic dose is usually 600-800 mg/day in 3 to 4 administrations. Although in some cases a dose of up to 1200 mg/day has been used and found to be more effective. Flavoxate is required to be administered three-four times a day, in some cases two tablets three to four times a day. This dosage regimen affects patient compliance and adds to pill burden thereby missing of doses that can affect the efficacy of the treatment. For indications which need chronic administration like urge incontinence and overactive bladder, three to four times a day therapy is highly unacceptable and inconvenient. The conventional IR dosage form poses risk of poor patient compliance; for instance, elder people forget to take the tablet(s) regularly, or there can be more serious risk of over-dosing by unknowingly consuming more than prescribed doses. Poor sleep, in elderly people also results from nocturia, which is frequently overlooked. IR tablets of Flavoxate consumed in evening time fail to cover the entire duration of sleep throughout night. The short half-life of Flavoxate further makes it impossible for a patient to ingest a dosage form containing a sufficient amount of the active in single administration to provide a therapeutic effect while the patient is asleep overnight. Thus, one of the major drawbacks of conventional IR tablets of Flavoxate is its dosage schedule.

Advantages of controlled or extended release (CR or ER) products are well known and documented in the pharmaceutical field. The advantages include, but not limited to, ability to maintain a desirable blood level of a medicament over an extended period by minimizing the peak to trough variations in plasma concentrations. Drug plasma levels of ER products are maintained within a narrow window with no sharp peaks and with AUC (Area under the curve) of plasma concentration v/s time curve comparable with total AUC obtained from multiple dosing of IR dosage form. This further avoids side effects associated with high concentration of drug released immediately in blood. Furthermore, ER products provide advantage of avoiding repeated administration throughout night time. This improves patient compliance and thereby improves the quality of life of the patient.

Flavoxate hydrochloride is a poorly soluble and a poorly compressible drug. Therefore, another challenge for the drug is to form compact orally-administrable tablets. In order to accommodate the required larger dosages, in an ingestible tablet form, the amount of controlled release polymers, binders and excipients have to be kept so low that final overall weight of the tablet does not exceed limit of practicality. Very large, non-chewable tablets cannot be ingested easily by elderly, much less by one in a weakened physical condition. Owing to the poor solubility of Flavoxate, delivery of an ER drug formulation has always been a challenge due to relatively large amounts of excipients generally needed to provide a specific delivery profile.

As already mentioned the major challenge with the design of oral dosage forms resides in their poor bioavailability. The oral bioavailability depends on several factors including aqueous solubility, drug permeability, dissolution rate, first-pass metabolism, pre-systemic metabolism, and susceptibility to efflux mechanisms. The most frequent causes of low oral bioavailability are attributed to poor solubility and low permeability.

JPS63154619A attempts to address the problem of administering Flavoxate hydrochloride employing delayed-release formulations. The Japanese patent application describes an ER formulation by preparing a fast-dissolving Flavoxate preparation and a slow dissolving Flavoxate preparation and blending them in a ratio of 1:0.5 to achieve release over twice the duration obtained by a 100 mg Flavoxate made by traditional IR methods. However, the pharmaceutical formulations of this patent application fail to provide 24-hour efficacy.

U.S. Pat. No. 9,750,701, provides achieving retarded release profiles of drugs such as Flavoxate by rendering anisotropic physical properties to tablets by providing indentations in the tablets.

Satyavathi et al. [K. Satyavathi, M. Venu, P. Gayathri, P. Bhojaraju and L. K. Kanthal, Formulation and development of Flavoxate hydrochloride ER capsules, IJPSR, 2014; Vol. 5(5): 1949-1956] describes making ER capsules of Flavoxate using ethyl cellulose and hydroxypropyl methyl cellulose, extruding them as pellets, drug-loading the pellets, and providing ER coating on the drug-laden pellets. Dissolution profiles show that the formulation is unable to provide 24-hour therapeutic coverage.

EP 0393572 A2, EP 0250374 B1 and U.S. Pat. Nos. 9,642,809 and 5,165,937, all of which have been incorporated by reference herein, have made attempts to provide controlled release of Flavoxate. U.S. Pat. No. 9,642,809 describes controlled release of the drug by incorporating it in a water-soluble micro-crystalline matrix. EP 0250374 B1 teaches a drug-excipient ratio of 60:40 that is unsuitable for single dose delivery of 600 mg or 800 mg Flavoxate.

EP 0393572 A2 and U.S. Pat. No. 5,165,937 suggest mandatory incorporation of acidifying agents (for instance, like tartaric acid or citric acid) among other additives and excipients in the oral dosage form for external diffusion of Flavoxate. Flavoxate is not very soluble in its unsalified form; it is advantageous to keep it salified while it is present in intestinal environment, where there is a tendency for gradual desalification to occur due to basic pH of the intestinal environment. The challenge for the formulation(s) of Flavoxate without acidifying agents is that Flavoxate is not very soluble in its unsalified form and an acidifying agent is needed to achieve Flavoxate in appropriate quantities and to facilitate controlled release of Flavoxate. A cross-over trial was conducted on six healthy adult volunteers who received 400 mg of CR tablets of Flavoxate hydrochloride. The duration of therapeutically effective levels of Flavoxate observed was 11.35 hours at plasma concentrations greater than or equal to 1 mcg/ml, this being the minimum effective value. Hence this trial is not suitable for making once a day preparation.

RASHID et al., 2021 [Development and evaluation of Flavoxate HCl double core compressed tablet formulations by swellable granulation technique. Acta Poloniae Pharmaceutica—Drug Research, Vol. 78 No. 5 667-677] describes development of double core differential release tablets of Flavoxate HCl. The article discloses incorporation of large quantity of Avicel PH 101 in outer core granule of Flavoxate HCl tablets. The article also discloses incorporation of citric acid as an essential ingredient in sustained release inner core when comprising HPMC K15. This article also discloses sustained release inner core with Kollidon SR and no HPMC K15. The article teaches either incorporation of acid or incorporation of large amount of excipients which will limit quantity of Flavoxate HCl to be incorporated for arriving at tablets having both; a size ensuring patient compliance and having Flavoxate HCl in quantities ensuring its sustained release through prolonged time period.

WO202021422A1 is the Applicant's another patent application which relates to a CR oral formulation comprising about 400 to 800 mg of Flavoxate salt as an active ingredient and wherein the oral formulation is free of acidifying agent as monolayer tablets. The application discloses preparation of monolayer tablets of reduced size with ER drug profile.

Oral studies in humans indicate that Flavoxate is readily absorbed from the intestine and converted, to a large extent, almost immediately to MFCA (3-methylflavone carboxylic acid). Both MFCA and Flavoxate inhibit cAMP-dependent phosphodiesterase, which is crucial for smooth muscle relaxation. Following an IV dose (equimolar to 100 mg), the following parameters were calculated for Flavoxate: $T_{1/2}$ 83.3 mins: apparent volume of distribution 2.89 l/kg. The apparent distribution of MFCA was 0.20 l/kg. No free Flavoxate was found in urine (24 hours). However, 47% of the dose was excreted as MFCA.

Following single oral dosing to volunteers of 200 mg and 400 mg Flavoxate, almost no free Flavoxate was detected in the plasma. The peak level of MFCA was attained at 30-60 minutes after the 200 mg dose and at around two hours following the 400 mg dose. The AUC for the 400 mg dose was approximately twice as large as the AUC for the 200 mg dose. About 50% of the dose was excreted as MFCA within 12 hours; most of which being excreted within the first 6 hours. After repeated oral dosing (200 mg, TDS, 7 days) the cumulative excretion of metabolites stabilized at 60% of the dose on the third day remaining almost unchanged after one week (Flavoxate hydrochloride 200 mg film-coated tablets, summary of product characteristics, is available on https://www.medicines.org.uk/emc/product/322/smpc).

The short half-life of Flavoxate makes it challenging to maintain effective therapeutic levels in circulation through a 24-hour period. The existing regimen of administering 100 or 200 mg of Flavoxate requires consumption of many tablets during the day resulting in reduced patient-compliance.

Flavoxate has very poor aqueous solubility which presents formulation problems owing to its slow rate of dissolution. Its efficacy can be severely limited and large inter individual variations of absorption can occur. Many techniques have been used to provide CR pharmaceutical dosage forms in order to maintain therapeutic serum levels of medicaments. However, for relatively water insoluble drugs such as Flavoxate, developing a CR formulation generally requires considerable experimentation because it is often not possible to readily predict whether a particular CR formulation will yield the desired modified release profile while also maintaining suitable handling properties such as sufficient tablet hardness and appropriate friability. Owing to the fact that water insoluble drugs tend to yield inconsistent drug release profiles, the task of preparing CR formulations of Flavoxate has proven difficult. The pharmacokinetic challenges are so substantial that, despite the passage of 50 years, the therapeutic dosage regimen has not significantly varied.

Poor solubility of Flavoxate hydrochloride in aqueous media likely results in lower dissolution or drug release in the lower part of the intestinal tract i.e. pH 5 to 7.4 range after oral administration, especially when this is formulated as ER solid dosage formulation.

Biphasic drug delivery system is known in the field of art as a drug delivery system for oral administration which is composed of one fast release or IR layer and one sustained release or CR layer. Layered tablet concept is utilized to develop CR and sustained release formulations. This system is typically used when maximum relief needs to be achieved quickly, followed by a sustained release phase to avoid repeated administration.

In the field of art 'layered tablet' form of Flavoxate or salt thereof are not known. Further the known processes for preparing layered tablets of other drugs employ divergent approaches and incorporate altogether different components in the formulation.

The therapeutic dose of Flavoxate is generally 600-800 mg/day and even in some cases a dose of up to 1200 mg/day may be required which is administered in multiple doses. Flavoxate hydrochloride has a very short half-life and duration of its therapeutic activity is about 5 to 6 hours. Thus, there is a need to develop a formulation which maintains the therapeutic effectiveness of the drug for a longer duration; reduces the frequency of administration; and thereby considerably improves patient compliance and quality of life of a patient.

Clearly, there is an unmet need for a CR drug delivery system that will ensure immediate and extended drug release profiles of Flavoxate to achieve the desired therapeutic plasma concentration over a 12-24 hours period as a single ingestible dosage form.

SUMMARY OF THE INVENTION

The present disclosure provides CR or ER release formulations or drug delivery systems comprising Flavoxate or salt thereof which provide once or twice a day therapy and effective plasma concentration for up to 12 to 24 hours. The present disclosure provides CR or ER formulations of Flavoxate or salt thereof as bi-layered, multi-layered tablets, multicoated mini-tablets, MUPS (Multiple Unit Pellet System) tablets, pellets or beads filled in capsules with biphasic drug release profile. The present disclosure also provides methods for preparation of such formulations and uses thereof.

In some embodiments, the ER formulations of Flavoxate or salt thereof provided are designed in such a way that sufficient amount of the drug is released immediately to achieve plasma levels similar to an IR dosage form, and the remaining drug is gradually released over extended period of time to maintain the drug concentration within the therapeutic window. Thus, the formulations provided herein provide a rapid and prolonged release of Flavoxate. In some embodiments, the Flavoxate ER formulations provided herein avoid fluctuations of plasma levels with reduced side effects due to a simplified dosage schedule, compared with those of IR dosage form, thereby improving patient compliance.

Accordingly, in an aspect the present disclosure provides formulations of Flavoxate which have improved patient compliance. The present disclosure in some embodiments provides a drug delivery system of Flavoxate that provides benefits of both IR and ER profiles; and simple and low-cost process for manufacturing this drug delivery system or formulation. In some embodiments, the CR or ER formulations of the present disclosure can be administered as a single ingestible dosage form and have improved bioavailability.

In another aspect, the present disclosure provides a simple and economical manufacturing process which provides a biphasic drug delivery system for Flavoxate; and develops bioavailable ER dosage form of Flavoxate which when orally administered will provide about 12 to about 24 hours therapeutic effect with adequate plasma levels.

ER formulations or drug delivery system of present disclosure provide sustained release profile for extended period of about 12 to about 24 hours and is suitable for being administered as a single ingestible dosage form. In some embodiments, formulations exhibit biphasic drug release profile whereby sufficient amount of the drug is released in initial hours to achieve plasma levels similar to conventional IR dosage form and rest of the drug is gradually released to maintain the drug concentration within therapeutic window.

In some embodiments, the formulations of present disclosure exhibit biphasic drug release profile whereby sufficient amount of the drug is released initially within 2 hours to achieve plasma levels similar to conventional IR dosage form and rest of the drug is gradually released over period of about 12 to about 24 hours to maintain the drug concentration within therapeutic window. In some embodiments, the developed formulations comprise about 10 to 30 wt % of IR drug layer and about 70 to 90 wt % of ER drug layer. In some embodiments, the ER formulations of present disclosure are developed by employing a careful selection of controlled release polymers resulting in formulations which may be manufactured into a commercially acceptable form, e.g. a tablet that shows unexpectedly good bioavailability of Flavoxate as well as a prolonged duration of action. This makes it possible to deliver therapeutic levels of drug for up to about 12 to about 24 hours in a recipient through a single dose administration.

The disclosure provides ER formulations as bi-layered, multi-layered tablets, multicoated mini-tablets, MUPS tablets, pellets or beads filled in capsules. In some embodiments, the ER formulations can be easily manufactured by direct compression, dry granulation, wet granulation, fluidized bed processing or hot melt granulation techniques.

Other aspects of the disclosure include methods of treating diseases or disorders responsive to Flavoxate, such as, e.g., disorders of the genitourinary tract, including but not limited to pollakiuria, nocturia, dysuria, urgency, vesicle suprapubic pain, frequency, urinary incontinence originating from various pathological conditions, such as prostatitis, urethritis, cystitis, urethero-cystitis, uretherotrigonitis, and side effects of radiotherapy or surgical therapy of the urinary tract; vesico-urethral spasm due to catheterization, cystoscopy, or indwelling catheter; irritative symptoms of benign prostatic hyperplasia (BPH) and overactive bladder; or as a preventative prior to cystoscopy, catheterization, or sequelae of surgical intervention of lower urinary tract.

In some embodiments, the present disclosure provides a controlled release oral formulation of Flavoxate with biphasic drug release profile comprising about 600 to 800 mg of Flavoxate salt as an active ingredient, at least one surfactant, and at least one polymer, wherein the surfactant has a hydrophilic-lipophilic balance value of at least '8'; wherein the formulation comprises at least one immediate release drug layer and at least one extended release drug layer; wherein the at least one immediate release drug layer is about 10 to 30 wt % of the formulation; and the at least one extended release drug layer is about 70 to 90 wt % of the formulation.

In some embodiments, the present disclosure provides a controlled release oral formulation of Flavoxate with biphasic drug release profile wherein on a single dose administration about 10% w/w to 35% w/w of the Flavoxate salt is released within an initial 2 hours, and the remaining Flavoxate salt is released for up to 12 to 24 hours.

In some embodiments, the present disclosure provides that the at least one polymer in the controlled release oral formulation comprises a hydrophilic cellulosic polymer or salt thereof, a hydrophobic cellulosic polymer or salt thereof, an ionic methacrylate copolymer or salt thereof, or a combination thereof.

In some embodiments, the present disclosure provides that the at least one polymer in the controlled release oral formulation comprises hydroxypropylmethyl cellulose (HPMC), hydroxy propyl methyl cellulose acetyl succinate (HPMC AS), Eudragit L30D 55, Eudragit L100, or a combination thereof.

In some embodiments, the present disclosure provides that the at least one surfactant in the controlled release oral formulation comprises a long alkyl chain sulfonate or a long alkyl chain sulfate, sodium dodecylbenzene sulfonate, sodium lauryl sulfate, dialkyl sodium sulfosuccinate, a quaternary ammonium salt, a fatty alcohol such as lauryl, cetyl, and steryl, glycerylesters, a fatty acid ester, a polyoxyethylene derivative of a fatty acid ester, or a combination thereof.

In some embodiments, the present disclosure provides that the at least one surfactant in the controlled release oral formulation comprises Polysorbate grades including Tween-20, Tween-80, or a combination thereof.

In some embodiments, the present disclosure provides that the controlled release oral formulation comprises at least one diluent, wherein the at least one diluent comprises mannitol, sorbitol, microcrystalline cellulose, lactose, dicalcium phosphate, starch, or a combination thereof.

In some embodiments, the present disclosure provides that the controlled release oral formulation comprises at least one binder, wherein the at least one binder comprises starch, polyvinylpyrrolidone, natural or synthetic gum, a cellulosic polymer, ethyl cellulose, hydroxypropylcellulose, gelatin, or a combination thereof.

In some embodiments, the present disclosure provides that the controlled release oral formulation comprises at least one disintegrant, wherein the at least one disintegrant comprises starch, sodium starch glycollate, croscarmellose sodium, crospovidone, or a combination thereof.

In some embodiments, the present disclosure provides that the controlled release oral formulation comprises at least one lubricant or glidant, wherein the at least one lubricant or glidant comprises talc, colloidal silicon dioxide, magnesium stearate, sodium stearyl fumarate, or a combination thereof.

In some embodiments, the present disclosure provides that the controlled release oral formulation releases Flavoxate salt throughout a course of 12 to 24 hours.

In some embodiments, the present disclosure provides that the Flavoxate salt in the controlled release oral formulation is Flavoxate hydrochloride.

In some embodiments, the present disclosure provides that the controlled release oral formulation is in a solid dosage form preferably a tablet or capsule.

In some embodiments, the present disclosure provides that the tablet is bi-layered, tri-layered or multi-layered tablet, multicoated mini-tablet, Multiple-Unit Pellet System tablets, pellets, or beads filled in capsules.

In some embodiments, the present disclosure provides that the tablet has a hardness of about 6 $kg/cm^2$ to about 40 $kg/cm^2$.

In some embodiments, the present disclosure provides that the tablet comprises one or more functional or non-functional coatings.

In some embodiments, the present disclosure provides that the functional film coating of the tablet is ethyl cellulose dispersion with soluble polymer or enteric polymer based dispersion with water soluble ingredients.

In some embodiments, the present disclosure provides that the non-functional film coating of the tablet is hydroxypropylmethyl cellulose based film coating dispersion with or without flavour to enhance the product acceptability of bitter tasting drugs.

In some embodiments, the present disclosure provides that the controlled release oral formulation releases between about 10% and about 35% of active ingredient during about 0 to 2 hours, between about 35% and about 75% of active ingredient during about 2 to 4 hours, between about 50% and about 90% of active ingredient during about 4 to 6 hours, and not less than about 75% during about 6 to 8 hours.

In some embodiments, the present disclosure provides a method of making a tablet with biphasic drug release profile comprising Flavoxate salt as an active ingredient, the method comprising:

(a) blending an amount of Flavoxate salt with an amount of suitable fillers, binders, surfactant, and controlled release polymers in suitable ratio of aqueous and organic solvent media to individually obtain blended material for immediate release or extended release layers;

(b) granulating blended material obtained in step (a) using suitable dry granulator or with a solution of binding polymer in non-aqueous or hydro alcoholic solvent using suitable granulation equipment to obtain granules;

(c) drying granules obtained in step (b) at a suitable temperature to obtain dried granules;

(d) screening dried granules obtained in step (c) through a mesh of appropriate size to obtain granules of desired size;

(e) lubricating granules obtained in step (d) with a soluble or insoluble lubricant to obtain formulation; and (f) compressing the formulation obtained in step (e) to form the tablet.

In some embodiments, the present disclosure provides that in the method said amount of Flavoxate salt is from about 100 mg to 200 mg for immediate release layer and from about 300 to 700 mg for extended release layer.

In some embodiments, the present disclosure provides that in the method said aqueous and organic solvent media in step (a) is water and isopropyl alcohol.

In some embodiments, the present disclosure provides that in the method suitable ratio of water and isopropyl alcohol is 70:30 and is about 30% w/v to 60% w/v of dry mix blend for immediate release layer and is about 40% w/v to 60% w/v of dry mix blend for immediate release layer.

In some embodiments, the present disclosure provides a method of making a tablet with biphasic drug release profile comprising about 600 mg to 800 mg of Flavoxate salt or similar lipophilic acid soluble drugs as an active ingredient, the method comprising:

(a) blending an amount of active ingredient, fillers, binders, and controlled release polymers to individually prepare immediate release or extended release layers; and (b) compressing individual layers to obtain tablets.

In some embodiments, the present disclosure provides that the method further comprises coating the tablet with or without one or more functional or non-functional coatings.

In some embodiments, the present disclosure provides that the tablet obtained by the method has hardness of from 6 $Kg/cm^2$ to 40 $Kg/cm^2$.

In some embodiments, the present disclosure provides that the tablet prepared by the method is bi-layered, tri-layered or multi-layered tablet, multicoated mini-tablet, Multiple-Unit Pellet System tablets, pellets, or beads filled in capsules.

In some embodiments, the present disclosure provides a method of treating and/or ameliorating at least one symptom of pollakiuria, nocturia, dysuria, urgency, vesicle suprapubic pain, frequency, urinary incontinence originating from various pathological situations such as prostatitis, urethritis, cystitis, urethero-cystitis, uretherotrigonitis, relief of vesico-urethral spasms due to catheterisation, cystoscopy or indwelling catheters; prior to cystoscopy or catheterisation; sequelae of surgical intervention of the lower urinary tract and/or the side effects of radiotherapy or surgical therapy of the urinary tract which comprises administering a formulation of present disclosure.

In some embodiments, the present disclosure provides use of the formulation for treatment or symptomatic relief of pollakiuria, nocturia, dysuria, urgency, vesicle suprapubic pain, frequency, urinary incontinence originating from various pathological conditions, such as prostatitis, urethritis, cystitis, urethero-cystitis, uretherotrigonitis, and side effects of radiotherapy or surgical therapy of the urinary tract; vesico-urethral spasm due to catheterization, cystoscopy, or indwelling catheter; irritative symptoms of benign prostatic hyperplasia (BPH) and overactive bladder; or as a preventative prior to cystoscopy, catheterization, or sequelae of surgical intervention of lower urinary tract.

DETAILED DESCRIPTION OF THE INVENTION

The terms “composition” and “formulation” are used interchangeably herein to refer to a Flavoxate hydrochloride containing drug product in a solid oral dosage form.

The terms “Flavoxate” and “Flavoxate hydrochloride” are used interchangeably to refer to the active ingredient in the compositions of the disclosure, 2-piperidinoethyl-3-methylflavone 8-carboxylate hydrochloride.

The term “controlled release” or “extended release” used throughout the specification shall apply to dosage forms, matrices, particles, coatings, portions thereof, or compositions that alter the release of an active ingredient in any manner. Types of controlled release include modified, prolonged, sustained, extended, delayed, and the like.

Preparing Flavoxate ER Formulations

As part of initial development plan, trials for selection of suitable sustained release polymers, binders, diluents, surfactants, disintegrants, lubricants and glidants were undertaken. The initial batches were prepared from group of suitable drug release polymers including but not limited to hydrophilic polymers and hydrophobic polymers or combination thereof.

The CR formulations of present disclosure employ CR polymers viz. non-ionic soluble cellulose, such as hypromellose, hydroxypropylmethyl cellulose (HPMC), hydroxypropylcellulose (HPC), carboxymethyl cellulose or salts of any of these polymers, hydroxylethylcellulose (HEC e.g., Natrosol™); non-ionic homopolymers of ethylene oxide, such as poly(ethylene oxide) with a molecular weight range of about 100,000 to 8000,000 Da; methyl cellulose; ethyl cellulose; water soluble natural gums of polysaccharides of natural origin or salts of any of these polymers, such as xanthum gum, karaya gum, sodium alginate, acrylic polymers, alginate, and locust bean gum; water-swellable but insoluble, high molecular weight homo-polymers and copolymers of acrylic acid chemically cross-linked with polyalkenyl alcohols with varying degree of cross-linking or particle size (for e.g. Carbopol® 71G NF, 971P, 934P); polyvinyl acetate and povidone mixture (for e.g. Kollidone® SR), cross-linked high amylose starch or ionic methacrylate copolymers (for e.g. Eudragit® L30D, Eudragit® L100 and Eudragit® L100 55); hyrdoxy propyl methyl cellulose phthalate (HPMCP); cellulose acetate phthalate (CAP) and hyrdoxy propyl methyl cellulose acetyl succinate (HPMCAS), alone or in combination. The CR formulation preferably employs different grades of HPMC and HPMC-AS alone or in combination as polymers. Among other things, formulations employing hydrophilic cellulosic polymers or salts thereof, hydrophobic cellulosic polymers or salts thereof, and/or ionic methacrylate copolymers or salts thereof, exhibit improved stability, dissolution profile, and bioavailability.

Flavoxate hydrochloride, being poorly water soluble, is employed with high load drug content. Based on initial studies, addition of pharmaceutically acceptable surfactants having a hydrophilic-lipophilic balance value (“HLB” i.e. the balance of the size and strength of the hydrophilic and lipophilic moieties of a surfactant molecule) of at least ‘8’ surprisingly leads to significant improvement in rate of dissolution in different physiological medias for Flavoxate. The suitable surfactants may, for example, be selected from long alkyl chain sulfonates or long alkyl chain sulfates such as sodium dodecylbenzene sulfonate, sodium lauryl sulfate, and dialkyl sodium sulfosuccinate, quaternary ammonium salts, fatty alcohols such as lauryl, cetyl, and steryl, glycerylesters, fatty acid esters, and polyoxyethylene derivatives of fatty acid esters, such as Polysorbates grades including polysorbate 20, polysorbate 60, and polysorbate 80 etc. or combination thereof. Different grades of polysorbates alone or in combination are the preferred surfactants. Among other things, formulations employing polysorbates exhibit improved stability, dissolution profile, and bioavailability.

Formulations employing both hydrophilic cellulosic polymers or salts thereof, hydrophobic cellulosic polymers or salts thereof, and/or ionic methacrylate copolymers or salts thereof, and polysorbates exhibit improved stability, dissolution profile, and bioavailability.

Additionally, the ER formulation may also contain “pharmaceutically acceptable excipients” selected from, for example, one or more of diluents, binders, disintegrants, lubricants and glidants.

The diluent may, for example, may be selected from, for example, one or more of mannitol, sorbitol, microcrystalline cellulose, lactose, dicalcium phosphate and starch etc.

The binder may be selected from, for example, one or more of starch, polyvinylpyrrolidone (PVP), natural or synthetic gum and cellulosic polymers e.g. ethyl cellulose, hydroxypropylcellulose (HPC), gelatin etc.

The disintegrants may be selected from, for example, one or more of starch, sodium starch glycollate, croscarmellose sodium or crospovidone etc.

The lubricants and glidants may be selected from, for example, one or more of talc, colloidal silicon dioxide, magnesium stearate or sodium stearyl fumarate etc.

The polymers and excipients used were selected on the basis of materials and their known properties and combined into a composition so as to incorporate 600 and 800 mg of drug for formulating different layers of proposed formulations in order to achieve appropriate hardness and thickness parameters during compression stage for respective strengths.

Various batches were investigated to arrive at a final formulation that is stable and exhibits a control or extended drug release profile. Even though some of the constituents of the formulation are already known in the art, yet no one to the knowledge of the inventors could develop a commercially acceptable form of CR formulation in multi-layered dosage forms that sustains therapeutic levels of the Flavoxate drug in plasma for up to 24 hours.

The ER formulations of Flavoxate can be obtained in form of tablets, beads, pellets or capsules. The tablets can be uncoated tablets, coated tablets, MUDS tablets or mini-tablets. For instance, the ER formulations can be a bi-layer, tri-layer or multi-layered tablets with or without one or more functional or non-functional coatings. A functional film coating is a coating that has a direct influence on the drug release of API (active pharmaceutical ingredient) of the solid oral dosage form (e.g. tablet, capsule, granule or pellet). The examples include, but not limited to, ethyl cellulose dispersion with soluble polymer or enteric polymer-based dispersion with water soluble ingredients. While a non-functional film coating does not directly influence the drug release of the API. The examples include, but not limited to, HPMC based film coating dispersion with or without flavour to enhance the product acceptability of bitter tasting drugs. The tablet can be prepared by direct compression, wet granulation, dry granulation or slugging or direct compression processes. The compressed tablets can be coated with suitable film forming compositions.

The disclosure is being illustrated herein below with examples of CR Flavoxate formulations in an easily-ingestible single tablet and process for preparation thereof is also provided herein below.

Manufacturing Procedure for Wet Granulation Method

The active ingredient, fillers, binders, surfactants and controlled release polymers were blended together for IR or ER layers, and then the blend milled through a screen with appropriate size mesh. The blended material was then granulated using suitable dry granulator or with a solution of binding polymer in non-aqueous or hydro alcoholic solvent using suitable granulation equipment. The granules were then dried at a suitable temperature and screened through a mesh of appropriate size. The blend was lubricated with a soluble or insoluble lubricant. The tablets were then formed by compression. The hardness of the tablet may vary from about 6 Kg/cm$^2$ to 40 Kg/cm$^2$ for tablets of different strengths.

From product design perspective, the ER Flavoxate hydrochloride formulation for oral administration comprises:

1) An IR layer comprising:
   (a) Flavoxate or pharmaceutically acceptable salts thereof;
   (b) suitable binder, polymer, surfactant, dissolved or dispersed in suitable ratio of aqueous and organic solvent media;
   (c) filler in appropriate concentrations intragranularly;
   (d) suitable disintegrant, flow aids or lubricants etc. extragranularly.
2) An ER layer comprising:
   (a) Flavoxate or pharmaceutically acceptable salts thereof;
   (b) suitable binder, surfactant, dissolved or dispersed in suitable ratio of aqueous and organic solvent media;
   (c) suitable ratios of polymers of different viscosity grades;
   (d) suitable flow aids, lubricants etc. extragranularly.
3) Compressed tablets are optionally coated with a suitable film coating material.

Manufacturing Procedure for Direct Compression Method

The present disclosure provides a process of preparing a pharmaceutical formulation of Flavoxate wherein the active ingredient, fillers, binders and controlled release polymers are blended together for individually preparing IR and ER layers. The individual layers are then compressed to form 600 or 800 mg bilayer tablets or tri-layer tablets of Flavoxate.

Examples for representative purpose without limiting scope of the disclosure are illustrated below.

EXAMPLE 1

Formulation of Biphasic Tablets Comprising 600 and 800 mg of Flavoxate Hydrochloride by Wet Granulation The Flavoxate, fillers, binders, surfactants and controlled release polymers in concentrations recited in Table 1 below were blended together for IR or ER layers to obtain a blended material. The blended material was milled through a screen with a mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 1

Constituents in biphasic 600 mg and 800 mg tablets of Flavoxate as prepared by wet granulation

| | 600 mg | | 800 mg | |
|---|---|---|---|---|
| Material | IR layer | ER layer | IR layer | ER layer |
| Flavoxate hydrochloride | 120.00 | 480.00 | 160.00 | 640.00 |
| Lactose | 14.775 | 2.44 | 19.70 | 3.25 |
| HPMC K15 | — | 43.88 | — | 58.50 |
| Colloidal silicon dioxide | — | 1.46 | — | 1.95 |
| Sodium starch glycolate | 3.75 | — | 5.00 | — |
| Brilliant blue | 0.75 | — | 1.00 | — |
| Hydroxypropyl cellulose | 6.00 | 27.375 | 8.00 | 36.50 |
| Tween 80 | — | 2.925 | — | 3.90 |
| Water* | QS | QS | QS | QS |

TABLE 1-continued

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |
| Talc | 1.50 | — | 2.00 | — |
| Magnesium stearate | 1.50 | 5.475 | 2.00 | 7.30 |

*IPA:water (70:30) quantity for ER portion was—55% w/v of dry mix blend.
IPA:water (70:30) quantity for IR portion was—58% w/v of dry mix blend.

EXAMPLE 2

Formulation of Biphasic Tablets Comprising 600 and 800 mg of Flavoxate Hydrochloride The Flavoxate, fillers, binders, surfactants and controlled release polymers in concentrations recited in Table 2 below were blended together for IR or ER layers to obtain a blended material. The blended material was milled through a screen with mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 2

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Flavoxate hydrochloride | 140.00 | 460.00 | 186.00 | 614.00 |
| Lactose | 14.775 | 2.44 | 19.70 | 3.25 |
| HPMCAS | — | 15.00 | | 20.00 |
| HPMC K4M | — | 15.00 | — | 20.00 |
| Carbopol ® 971 | | 13.88 | | 18.50 |
| Colloidal silicon dioxide | — | 1.46 | — | 1.95 |
| Sodium starch glycolate | 3.75 | — | 5.00 | — |
| Brilliant blue | 0.75 | — | 1.00 | — |
| Ethyl cellulose | 6.00 | 27.375 | 8.00 | 36.50 |
| Tween 80 | — | 2.925 | — | 3.90 |
| Water* | QS | QS | QS | QS |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |
| Talc | 1.50 | — | 2.00 | — |
| Magnesium stearate | 1.50 | 5.475 | 2.00 | 7.30 |

*IPA:water (70:30) quantity for ER portion was—54% w/v of dry mix blend.
IPA:water (70:30) quantity for IR portion was—47% w/v of dry mix blend.

EXAMPLE 3

Formulation of Biphasic Tablets Comprising 600 and 800 mg of Flavoxate Hydrochloride The Flavoxate, fillers, binders, surfactants and CR polymers in concentrations recited in Table 3 below were blended together for IR or ER layers to obtain a blended material. The blended material was milled through a screen with mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 3

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Flavoxate hydrochloride | 135.975 | 468.45 | 181.30 | 624.60 |
| Lactose | 14.775 | 12.44 | 19.70 | 3.25 |
| Hydroxypropyl cellulose | — | 10.00 | — | 40.00 |
| Xanthan gum | | 10.88 | | 18.50 |
| Colloidal silicon dioxide | — | 1.46 | — | 1.95 |
| Sodium starch glycolate | 3.75 | — | 5.00 | — |
| Brilliant blue | 0.75 | — | 1.00 | — |
| PVP K 30 | 6.00 | 27.375 | 8.00 | 36.50 |
| Sodium lauryl sulphate | — | 2.925 | — | 3.90 |
| Water* | QS | QS | QS | QS |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |
| Talc | 1.50 | — | 2.00 | — |
| Magnesium stearate | 1.50 | 5.475 | 2.00 | 7.30 |

*IPA:water (70:30) quantity for ER portion was—45% w/v of dry mix blend.
IPA:water (70:30) quantity for IR portion was—35% w/v of dry mix blend.

EXAMPLE 4

Formulation of Biphasic Tablets Comprising 600 and 800 mg of Flavoxate Hydrochloride The Flavoxate, fillers, binders, surfactants and controlled release polymers in concentrations recited in Table 4 below were blended together for IR or ER layers to obtain a blended material. The blended material was milled through a screen with mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 4

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Flavoxate hydrochloride | 120.00 | 480.00 | 160.00 | 640.00 |
| Lactose | 14.775 | 5.44 | 19.70 | 6.25 |
| Eudragit L30D 55 | — | 20.00 | | 30.00 |
| Ethyl cellulose | — | 20.88 | — | 25.50 |
| Colloidal silicon dioxide | — | 1.46 | — | 1.95 |
| Crospovidone | 3.75 | — | 5.00 | — |
| Brilliant blue | 0.75 | — | 1.00 | — |
| Hydroxypropyl cellulose | 6.00 | 27.375 | 8.00 | 36.50 |
| Tween 80 | — | 2.925 | — | 3.90 |
| Water* | QS | QS | QS | QS |

TABLE 4-continued

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |
| Talc | 1.50 | — | 2.00 | — |
| Magnesium stearate | 1.50 | 5.475 | 2.00 | 7.30 |

*IPA:water (70:30) quantity for ER portion was—55% w/v of dry mix blend.
IPA:water (70:30) quantity for IR portion was—58% w/v of dry mix blend.

EXAMPLE 5

Formulation of Biphasic Tablets Comprising 600 and 800 mg of Flavoxate Hydrochloride The Flavoxate, fillers, binders, surfactants and controlled release polymers in concentrations recited in Table 5 below were blended together for IR or ER layers to obtain a blended material. The blended material was milled through a screen with mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 5

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Flavoxate hydrochloride | 140.00 | 460.00 | 186.00 | 614.00 |
| Lactose | 14.775 | 12.44 | 19.70 | 13.25 |
| HPMC K15M | — | 20.00 | — | 30.00 |
| Carbopol ® 971 | | 13.88 | | 18.50 |
| Colloidal silicon dioxide | — | 1.46 | — | 1.95 |
| Sodium starch glycolate | 3.75 | — | 5.00 | — |
| Brilliant blue | 0.75 | — | 1.00 | — |
| Ethyl cellulose | 6.00 | 27.375 | 8.00 | 36.50 |
| Tween 80 | — | 2.925 | — | 3.90 |
| Water* | QS | QS | QS | QS |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |
| Talc | 1.50 | — | 2.00 | — |
| Magnesium stearate | 1.50 | 5.475 | 2.00 | 7.30 |

EXAMPLE 6

Formulation of Biphasic Tablets Comprising 600 and 800 mg of Flavoxate Hydrochloride The Flavoxate, fillers, binders, surfactants and controlled release polymers in concentrations recited in Table 6 below were blended together for IR or ER layers to obtain a blended material. The blended material was milled through a screen with mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 6

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Flavoxate hydrochloride | 120.00 | 480.00 | 160.00 | 640.00 |
| Microcrystalline cellulose | 13.00 | 2.44 | 17.70 | 3.25 |
| HPMC K15 | — | 43.88 | — | 58.50 |
| Colloidal silicon dioxide | — | 1.46 | — | 1.95 |
| Croscarmellose sodium | 5.53 | — | 7.00 | — |
| Brilliant blue | 0.75 | — | 1.00 | — |
| Hydroxypropyl cellulose | 6.00 | 27.375 | 8.00 | 36.50 |
| Tween 80 | — | 2.925 | — | 3.90 |
| Water* | QS | QS | QS | QS |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |
| Talc | 1.50 | — | 2.00 | — |
| Sodium stearyl fumarate | 1.50 | 5.475 | 2.00 | 7.30 |

*IPA:water (70:30) quantity for ER portion was—55% w/v of dry mix blend.
IPA:water (70:30) quantity for IR portion was—58% w/v of dry mix blend.

EXAMPLE 7

Formulation of Biphasic Tablets Comprising 600 and 800 mg of Flavoxate Hydrochloride The Flavoxate, fillers, binders, surfactants and controlled release polymers in concentrations recited in Table 7 below were blended together for IR or ER layers to obtain a blended material. The blended material was milled through a screen with mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 7

| Constituents in biphasic 600 mg and 800 mg tablets of Flavoxate as prepared by wet granulation | | | | |
|---|---|---|---|---|
| | 600 mg | | 800 mg | |
| Material | IR layer | ER layer | IR layer | ER layer |
| Flavoxate hydrochloride | 120.00 | 480.00 | 160.00 | 640.00 |
| Microcrystalline cellulose | 13.00 | 2.44 | 17.70 | 3.25 |
| Eudragit L100 | — | 20.00 | | 30.00 |
| HPMC K15 | — | 23.88 | — | 28.50 |
| Colloidal silicon dioxide | — | 1.46 | — | 1.95 |
| Crospovidone | 5.53 | — | 7.00 | — |
| Brilliant blue | 0.75 | — | 1.00 | — |
| Hydroxypropyl cellulose | 6.00 | 27.375 | 8.00 | 36.50 |
| Tween 80 | — | 2.925 | — | 3.90 |
| Water* | QS | QS | QS | QS |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |

TABLE 7-continued

Constituents in biphasic 600 mg and 800 mg tablets of Flavoxate as prepared by wet granulation

| | 600 mg | | 800 mg | |
|---|---|---|---|---|
| Material | IR layer | ER layer | IR layer | ER layer |
| Talc | 1.50 | — | 2.00 | — |
| Sodium stearyl fumarate | 1.50 | 5.475 | 2.00 | 7.30 |

*IPA:water (70:30) quantity for ER portion was—55% w/v of dry mix blend.
IPA:water (70:30) quantity for IR portion was—58% w/v of dry mix blend.

EXAMPLE 8

Formulation of Biphasic Tablets Comprising 600 and 800 mg of Flavoxate Hydrochloride The Flavoxate, fillers, binders, surfactants and controlled release polymers in concentrations recited in Table 8 below were blended together for IR or ER layers to obtain a blended material. The blended material was milled through a screen with mesh of appropriate size. The blended material was then granulated. The granules were then dried at a suitable temperature and screened through a mesh of appropriate size. The blend was lubricated with a soluble or insoluble lubricant. The tablets were then formed by compression. The hardness of the tablet was adjusted from 6 Kg/cm$^2$ to 40 Kg/cm$^2$ for tablets of different strengths.

TABLE 8

Constituents in biphasic 600 mg and 800 mg tablets of Flavoxate as prepared by wet granulation

| | 600 mg | | 800 mg | |
|---|---|---|---|---|
| Material | IR layer | ER layer | IR layer | ER layer |
| Flavoxate hydrochloride | 120.00 | 480.00 | 160.00 | 640.00 |
| HPMCAS | — | 30.00 | | 40.00 |
| Starch | 14.00 | 2.44 | 18.70 | 3.25 |
| HPMC K15 | — | 13.88 | — | 18.50 |
| Colloidal silicon dioxide | — | 1.46 | — | 1.95 |
| Croscarmellose sodium | 4.53 | — | 6.00 | — |
| Brilliant blue | 0.75 | — | 1.00 | — |
| Hydroxypropyl cellulose | 6.00 | 27.375 | 8.00 | 36.50 |
| Tween 80 | — | 2.925 | — | 3.90 |
| Water* | QS | QS | QS | QS |
| Isopropyl alcohol (IPA)* | QS | QS | QS | QS |
| MCC PH 102 | 7.50 | 4.50 | 10.00 | 6.00 |
| Colloidal silicon dioxide | — | 2.25 | — | 3.00 |
| Brilliant blue | 0.75 | — | 1.00 | — |
| Talc | 1.50 | — | 2.00 | — |
| Magnesium stearate | 1.50 | 5.475 | 2.00 | 7.30 |

*IPA:water (70:30) quantity for ER portion was—55% w/v of dry mix blend.
IPA:water (70:30) quantity for IR portion was—58% w/v of dry mix blend.

EXAMPLE 9

Formulation of ER Capsule Comprising 600 mg of Flavoxate Hydrochloride

The drug loaded drug pellets were produced by coating of Flavoxate along with ethyl cellulose, HPMC K4M, Talc and polysorbate 80 on MCC spheres using fluidized bed process to product CR pellets of Flavoxate. The coated pellets were then appropriately lubricated with extragranular contents as recited in Table 9. The coated drug pellets were filled in capsules of gelatin (hard or soft) and non-gelatin capsule shells (e.g., HPMC or sodium alginate vegetarian capsules).

TABLE 9

Constituents in 600 mg capsule of Flavoxate as prepared by wet granulation
MUPS Capsules

| Ingredient | Qty Per unit (in mg) |
|---|---|
| Flavoxate hydrochloride | 600.00 |
| HPMC K4M | 12.00 |
| Cellulose acetate phthalate | 10.00 |
| Polysorbate 80 | 12.00 |
| Talc | 5.00 |
| Microcrystalline cellulose spheres 355-425 μm | 40.00 |
| Ethyl cellulose coating dispersion | 20.00 |
| Microcrystalline cellulose | 93.00 |
| Magnesium stearate | 4.00 |
| Colloidal silicon dioxide | 4.00 |

EXAMPLE 10

Formulation of ER MUPS Tablets Comprising 600 mg of Flavoxate Hydrochloride

MUPS tablets were produced by compressing a mixture of Flavoxate containing pellets and powder excipients in concentration as provided in Table 10 below. The pellets have a spherical core that contains or is optionally coated with the Flavoxate and one or more protective layers to control drug release.

TABLE 10

Constituents in 600 mg MUPS tablets of Flavoxate as prepared by wet granulation method
MUPS Tablets

| Ingredient | Qty Per unit (in mg) |
|---|---|
| Flavoxate hydrochloride | 600.00 |
| HPMC phthalate | 6.00 |
| HPMC K15M | 6.00 |
| Polysorbate-80 | 12.00 |
| Talc | 5.00 |
| Sugar spheres 355-425 μm | 50.00 |
| Ethyl cellulose coating dispersion | 20.00 |
| Microcrystalline cellulose | 93.00 |
| Magnesium stearate | 4.00 |
| Colloidal silicon dioxide | 4.00 |

EXAMPLE 11

In-vitro Dissolution Drug Release Profile

A representative in-vitro drug dissolution release rate profile for the formulation of Example 1 in pH gradient dissolution studies (every 2 hours in pH 1.2, pH 4.5, pH 6.8 and pH 7.4 respectively for total period of 8 hours) in simulating physiological pH media when product is dosed orally is presented herein below (Table 11).

TABLE 11

In-vitro dissolution drug release profile in simulated physiological pH conditions for the formulation of Example 1

| pH dissolution media | Time duration | % Cumulative drug release range |
|---|---|---|
| pH 1.2, 0.1N Hydrochloric acid | 0-2 hours | 10-35 |
| pH 4.5, Acetate buffer | 2-4 hours | 35-75 |

TABLE 11-continued

| In-vitro dissolution drug release profile in simulated physiological pH conditions for the formulation of Example 1 | | |
|---|---|---|
| pH dissolution media | Time duration | % Cumulative drug release range |
| pH 6.8, Phosphate buffer | 4-6 hours | 50-90 |
| pH 7.4, Phosphate buffer | 6-8 hours | NLT 75% |

The in-vitro dissolution release profile of ER formulations is found to be between about 10% and about 35% released during about 0 to 2 hours, between about 35% and about 75% released during about 2 to 4 hours, between about 50% and about 90% released during about 4-6 hours, and not less than (NLT) about 75% during about 6 to 8 hours.

EXAMPLE 12

Comparative Evaluation of In Vitro Dissolution Drug Release Profile of the Formulation of WO202021422A1 Versus Formulation of Example 1

The formulation of Example 1 was evaluated vis-à-vis the formulations disclosed in WO202021422A1 using in-vitro drug dissolution methodology as part of simulation study with human GIT using pH gradient dissolution medias (every 2 hours in pH 1.2, pH 4.5, pH 6.8 and pH 7.4 respectively for total period of 8 hours) in simulating physiological pH media when product is dosed orally is presented herein below along with 24 hours dissolution study profile (Tables 12 and 13).

TABLE 12

| In-vitro dissolution drug release profile in simulated physiological pH conditions | | |
|---|---|---|
| Dissolution media (pH) | Example 1 Formulation % Cumulative drug release | WO202021422A1 |
| 0.1N Hydrochloric acid (0-2 hours) | 30 | 16 |
| 4.5 pH Acetate buffer (2-4 hours) | 67 | 37 |
| 6.8 pH Phosphate buffer (4-6 hours) | 84 | 53 |
| 7.4 pH Phosphate buffer (6-8 hours) | 93 | 68 |

TABLE 13

| Comparative 24 hours dissolution profile study of Example 1 and formulations of WO202021422A1 | | |
|---|---|---|
| 24 hours dissolution profile study Time in hours | Example 1 Formulation % Drug released | WO202021422A1 % Drug released |
| 2 | 28 | 11 |
| 4 | 44 | 25 |
| 6 | 57 | 41 |
| 8 | 69 | 56 |
| 10 | 80 | 66 |
| 12 | 89 | 77 |
| 14 | 96 | 89 |
| 16 | 100 | 99 |
| 24 | 100 | 100 |

It is evident from above Table 13 that the formulation of Example 1 has improved drug dissolution release at each pH evaluation stages indicating improved drug release profiles in both 8 hours pH gradient and 24 hours dissolution profile studies.

EXAMPLE 13

Comparative Study for In Vivo % Bioavailability of Exemplary Formulations of the Present Disclosure Versus Immediate Release Tablets 18 male participants between the age of 18-45 years (both inclusive) were administered either the Example 1 formulation or the reference IR formulation [Urispas® (Flavoxate HCl, 200 mg)]. All participants fasted for at least 10 hours before administration and then the test formulation was administered with water. Participants received either one extended release tablet of 600 mg strength as prepared in Example 1, or three IR tablets of 200 mg strength. One IR tablet was administered every 8 hours (i.e., at 0 hours, 8 hours, and 16 hours). Blood samples were collected from the participants at the several time points up to 24 hours, and the comparative plasma concentration at given times is shown in Table 14.

TABLE 14

| Comparative blood concentration for formulation of Example 1 and immediate release formulation | | |
|---|---|---|
| Time (in hrs) | 200 mg × 3 tablets (μg/ml) | 600 mg (μg/ml) |
| 0 | 0 | 0 |
| 0.333 | 2.1 | 3.2 |
| 0.667 | 3.6 | 6.9 |
| 1 | 3.1 | 6.1 |
| 1.333 | 2.7 | 5.6 |
| 1.667 | 2.2 | 5.4 |
| 2 | 1.9 | 5.3 |
| 2.333 | | 4.6 |
| 2.5 | 1.5 | |
| 2.667 | | 4.7 |
| 3 | 1.2 | 4.2 |
| 3.5 | | 3.3 |
| 4 | 0.9 | 2.5 |
| 5 | | 1.6 |
| 6 | 0.5 | 1.4 |
| 8 | 0.2 | 0.8 |
| 10 | 4.3 | 0.9 |
| 12 | 2.1 | 0.9 |
| 16 | 0.4 | 0.4 |
| 24 | 0.6 | 0.10 |

Further, the percentage (%) bioavailability of the formulation in Example 1 was evaluated vis-à-vis an immediate release formulation [Urispas® (Flavoxate HCl, 200 mg)] (Table 15) in terms of AUC (Area Under the curve).

TABLE 15

| Comparative % bioavailability [as AUC (Area under curve) parameter] for formulation of Example 1 and immediate release formulation | | |
|---|---|---|
| Parameter | BA of Example 1/BA of Ref. IR (in %) | Acceptance criteria (in %) |
| $AUC_{24}$[90% CI] | 78.03 [67.71-89.93] | 80-125 |

TABLE 15-continued

| Comparative % bioavailability [as AUC (Area under curve) parameter] for formulation of Example 1 and immediate release formulation | | |
|---|---|---|
| Parameter | BA of Example 1/BA of Ref. IR (in %) | Acceptance criteria (in %) |
| $AUC_{inf}$ [90% CI] | 69.52 [55.48-87.11] | 80-125 |
| Intra-subject % CV[ISCV] | 25.536/41.597 | — |

CI = confidence intervals
ISCV = intra-subject variability

EXAMPLE 14

In-vitro Dissolution Profile of Exemplary Formulations of Example 1 Versus Immediate Release Tablets Based on results of comparative studies of Example 13 the formulation of Example 1 was fine-tuned to arrive at the formulation of Example 8. The in-vitro dissolution profile of each formulation was studied. Comparative in-vitro dissolution profile in biorelevant dissolution test method for the tablets prepared by formulation of Example 8 was studied at pH 1.2 for first 2 hours followed by pH 7.4 buffer until 24 hours (Table 16).

TABLE 16

Comparative in-vitro dissolution profile for formulations of Example 1 and Example 8 Dissolution study [pH 1.2 for 1st 2 hours followed by pH 7.4 buffer until 24 hours] (in hrs.)

| | Batch/time | | | | | | | | | | | |
|---|---|---|---|---|---|---|---|---|---|---|---|---|
| | 0.5 | 1 | 2 | 3 | 4 | 6 | 8 | 10 | 12 | 16 | 20 | 24 |
| Example 1 (tested in BA study) | 9 | 22 | 35 | 30 | 31 | 32 | 34 | 35 | 36 | 39 | 40 | 41 |
| Example 8 (for further BA study) | 31 | 37 | 49 | 54 | 61 | 61 | 62 | 66 | 66 | 66 | 68 | 68 |

As is evident from the results of Table 16 above, tablet prepared by the formulation of Example 8 exhibits improved release profile relative to the formulation of Example 1.

EXAMPLE 15

Stability Data

The developed ER pharmaceutical formulations of Flavoxate or salt thereof in Example 1 and Example 8 demonstrate good chemical stability as per accelerated stability data. The developed formulations have improved chemical stability wherein individual unknown impurity levels are less than 0.2% w/w (as per currently available globally acceptable standards for drug products).

The stable ER or CR formulations and methods for preparation thereof as set forth in the present application accurately describe the efficacy and utility of these formulations and methods for preparation thereof to restore healthy functioning in humans and treat the conditions and disorders in humans as identified and described in this patent application.

Although the subject matter has been described herein with reference to certain preferred embodiments thereof, other embodiments are possible. For illustrative purpose, the formulations comprise Flavoxate hydrochloride as the active ingredient. However, those skilled in the art would appreciate that scope of the disclosure would extend to other similar lipophilic acid soluble drugs known in the field of art.

Other embodiments will be apparent to those skilled in the art from consideration of the specification and practice of the embodiments disclosed herein. It is intended that the specification and examples be considered as exemplary only, with a true scope and spirit of the disclosure being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herein below not be construed as being order-specific unless such order specificity is expressly stated in the claim.

Scope of the disclosure is thus indicated by the appended claims rather than by the foregoing description, and all changes that come within the meaning and range of equivalency of the claims are intended to be embraced therein.

What is claimed is:

1. A controlled release oral formulation of Flavoxate with biphasic drug release profile comprising:
- about 600 to 800 mg of Flavoxate salt as an active ingredient,
- at least one surfactant, and at least one polymer,
- wherein the surfactant has a hydrophilic-lipophilic balance value of at least '8';
- wherein the formulation comprises at least one immediate release drug layer and at least one extended release drug layer;
- wherein the at least one immediate release drug layer is about 10 to 30 wt % of the formulation; and
- the at least one extended release drug layer is about 70 to 90 wt % of the formulation.

2. The controlled release oral formulation as claimed in claim 1, wherein on a single dose administration about 10% w/w to 35% w/w of the Flavoxate salt is released within an initial 2 hours, and the remaining Flavoxate salt is released for up to 12 to 24 hours.

3. The controlled release oral formulation as claimed in claim 1, wherein the at least one polymer comprises a hydrophilic cellulosic polymer or salt thereof, a hydrophobic cellulosic polymer or salt thereof, an ionic methacrylate copolymer or salt thereof, or a combination thereof.

4. The controlled release oral formulation as claimed in claim 3, wherein the at least one polymer comprises hydroxypropylmethyl cellulose (HPMC), hydroxy propyl methyl cellulose acetyl succinate (HPMC AS), an ionic methacrylate copolymer or salt thereof, or a combination thereof.

5. The controlled release oral formulation as claimed in claim 1, wherein the at least one surfactant comprises a long alkyl chain sulfonate or long alkyl chain sulfate, sodium dodecylbenzene sulfonate, sodium lauryl sulfate, dialkyl sodium sulfosuccinate, quaternary ammonium salt, a fatty alcohol such as lauryl, cetyl, and steryl, glycerylesters, a fatty acid ester, a polyoxyethylene derivatives of a fatty acid ester, or a combination thereof.

6. The controlled release oral formulation as claimed in claim 5 wherein the at least one surfactant comprises Polysorbate grades including Tween-20, Tween-80, or a combination thereof.

7. The controlled release oral formulation as claimed in claim 1, further comprising at least one diluent, wherein the at least one diluent comprises mannitol, sorbitol, microcrystalline cellulose, lactose, dicalcium phosphate, starch, or a combination thereof.

8. The controlled release oral formulation as claimed in claim 1, further comprising at least one binder, wherein the at least one binder comprises starch, polyvinylpyrrolidone, natural or synthetic gum, a cellulosic polymer, ethyl cellulose, hydroxypropylcellulose, gelatin, or a combination thereof.

9. The controlled release oral formulation as claimed in claim 1, further comprising at least one disintegrant, wherein the at least one disintegrant comprises starch, sodium starch glycollate, croscarmellose sodium, crospovidone, or a combination thereof.

10. The controlled release oral formulation as claimed in claim 1, further comprising at least one lubricant or glidant, wherein the at least one lubricant or glidant comprises talc, colloidal silicon dioxide, magnesium stearate, sodium stearyl fumarate, or a combination thereof.

11. The controlled release oral formulation as claimed in claim 1, wherein the Flavoxate salt is Flavoxate hydrochloride.

12. The controlled release oral formulation as claimed in claim 1, wherein the formulation is in a solid dosage form, wherein the solid dosage form has a hardness of about 6 $kg/cm^2$ to about 40 $kg/cm^2$.

13. The controlled release oral formulation as claimed in claim 1, wherein the formulation releases:

between about 10% and about 35% of active ingredient during about 0 to 2 hours, between about 35% and about 75% of active ingredient during about 2 to 4 hours, between about 50% and about 90% of active ingredient during about 4 to 6 hours, and not less than about 75% during about 6 to 8 hours.

* * * * *